(12) United States Patent
Bills (10) Patent No.: US 7,357,789 B2
(45) Date of Patent: Apr. 15, 2008

(54) SPECIALLY DESIGNED SYRINGES FOR DISPENSING GRANULAR OR POWDERED SOLIDS

(75) Inventor: Dan J. Bills, Salt Lake City, UT (US)

(73) Assignee: Ultradent Products, Inc., South Jordan, UT (US)

( * ) Notice: Subject to any disclaimer, the term of this patent is extended or adjusted under 35 U.S.C. 154(b) by 227 days.

(21) Appl. No.: 10/995,571

(22) Filed: Nov. 23, 2004

(65) Prior Publication Data

US 2006/0116642 A1    Jun. 1, 2006

(51) Int. Cl.
*A61M 5/00* (2006.01)

(52) U.S. Cl. .................. 604/187; 604/192; 604/500

(58) Field of Classification Search ............. 604/110, 604/181, 187, 192, 197, 198, 500, 506, 199
See application file for complete search history.

(56) References Cited

U.S. PATENT DOCUMENTS

| | | | |
|---|---|---|---|
| 1,608,275 A | 11/1926 | Grier et al. | |
| 3,297,031 A | 1/1967 | Bray | 128/264 |
| 3,684,136 A | 8/1972 | Baumann | 222/386 |
| 3,739,947 A | 6/1973 | Baumann et al. | 222/136 |
| 4,551,135 A | 11/1985 | Gorman et al. | 604/82 |
| 4,562,844 A | 1/1986 | Carpenter et al. | 128/675 |
| 4,648,532 A | 3/1987 | Green | 222/82 |
| 4,769,011 A | 9/1988 | Swaniger | 604/218 |
| 4,801,263 A | 1/1989 | Clark | 433/90 |
| 4,909,250 A | 3/1990 | Smith | 606/117 |
| 4,966,601 A | 10/1990 | Draenert | 606/92 |
| 5,181,918 A | 1/1993 | Brandhorst et al. | 606/92 |
| 5,193,907 A | 3/1993 | Faccioli et al. | 366/130 |
| 5,314,416 A | 5/1994 | Lewis | 604/219 |
| 5,490,841 A * | 2/1996 | Landis | 604/110 |
| 6,171,285 B1 | 1/2001 | Johnson | 604/195 |
| 6,431,743 B1 * | 8/2002 | Mizutani et al. | 366/189 |
| 6,554,803 B1 * | 4/2003 | Ashman | 604/218 |
| 6,626,912 B2 | 9/2003 | Speitling | 606/92 |
| 2004/0030345 A1 | 2/2004 | Aurin et al. | 606/92 |
| 2004/0044318 A1 * | 3/2004 | Fiser et al. | 604/263 |

* cited by examiner

*Primary Examiner*—Kevin C. Sirmons
*Assistant Examiner*—Bhisma Mehta
(74) *Attorney, Agent, or Firm*—Workman Nydegger (57) ABSTRACT

An apparatus and method for delivering a granular or powdered material, e.g., a bone growth promoting material. The inventive syringe apparatus includes a syringe barrel having a proximal and distal end, a lid attached to the syringe barrel that is selectively movable between an open and closed position relative to the syringe barrel, and biasing means for biasing the lid toward a closed position relative to the syringe barrel. The biasing means may comprise a leaf spring, coiled spring, or elastomeric material. The syringe barrel may be straight or curved.

24 Claims, 6 Drawing Sheets

SPECIALLY DESIGNED SYRINGES FOR DISPENSING GRANULAR OR POWDERED SOLIDS

BACKGROUND OF THE INVENTION

1. The Field of the Invention

The present invention relates to apparatus and systems for delivering granular or powdered materials, e.g., those used for promoting and supporting bone growth.

2. The Relevant Technology

In dental work, it is often necessary to remove a tooth. Because the teeth are anchored to the jaw bone, removal of the tooth leaves a large discontinuity or defect in the bone once occupied by the tooth root. In some cases, certain tooth extractions may require the removal of surrounding bone tissue. Whereas the body is, in theory, capable of growing new bone to fill in the discontinuity or defect, bone typically grows very slowly. In fact, bone grows much more slowly than soft tissue, which preferentially grows and fills in much of the void, leaving a weakened, defective bone that is more prone to fracture or failure, particularly in the elderly. Secondarily, once a tooth has been removed, the surrounding jaw bone can atrophy and weaken as a result of non-use in the area of the removed tooth.

In order to restore or augment areas where bone has been removed, naturally derived and synthetically manufactured granular and powdered bone mineral substitutes have been developed. These materials are often used to preserve or augment the alveolar portion of the jaw bone that supports the teeth, augment atrophic alveolar ridges (e.g. tooth socket bones which have decreased in size as a result of tooth removal), and to fill various periodontal defects. Under one current practice, bone mineral substitutes for promoting bone growth in the form of granules or powders are manually delivered into the intended site using a spatula, spoon or other tool. This method often results in inadvertent spillage and placement of particles into unintended locations and in a general difficulty in filling the augmentation site as intended. This is especially the case when attempting to augment bone growth along a ridge, such as the alveolar ridge mentioned above.

In view of the foregoing, it would be an improvement in the art to provide improved delivery apparatus and methods to overcome the aforementioned difficulties.

BRIEF SUMMARY OF THE PREFFERED EMBODIMENTS

The present invention generally relates to apparatus and methods for delivering a granular or powdered material. The inventive syringe apparatus includes a syringe barrel having a proximal and distal end, a lid attached to the syringe barrel that is selectively movable between an open and closed position relative to the syringe barrel, and biasing means for biasing the lid toward a closed position relative to the syringe barrel.

According to one embodiment, the syringe barrel may be curved. Curving the barrel of the syringe allows for better maneuverability of the syringe apparatus within the mouth of a patient. This allows the user to more easily maneuver and deliver granules or powder material to the desired location.

The syringe includes a lid attached to the syringe barrel. The lid is selectively movable between an open and closed position relative to the syringe barrel. According to one embodiment, the lid may include a plurality of openings for allowing a user to suction blood or other liquid into the syringe barrel for mixing with the granular or powdered material prior to delivering the material to a desired location. According to one embodiment, the openings may comprise grooves formed in the lid.

The syringe further includes biasing means for biasing the lid toward the closed position relative to the syringe barrel. According to one embodiment, the biasing means comprises a leaf spring. By increasing the effective length of the leaf spring, the lid is forced to an open position, allowing the user to deliver the granular or powdered bone growth promoting material. According to another embodiment, the syringe apparatus may further include means for remotely manipulating the leaf spring (e.g., a pull-strap attached to an end of the leaf spring and selectively manipulated near the proximal end of the syringe barrel) so as to move the lid to an open position relative to the syringe barrel.

According to one embodiment, the syringe apparatus further includes a plunger. The plunger may be flexible. The plunger may advantageously have flexibility in both the x plane and the y plane. The plunger may also be curved, which is advantageous in embodiments where the syringe barrel is also curved.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

The present invention relates to a syringe apparatus and related method for delivering a granular or powdered material. The inventive syringe apparatus includes a syringe barrel having a proximal end and a distal end, a lid attached to the syringe barrel that is selectively movable between an open and closed position relative to the syringe barrel, and biasing means for biasing the lid toward a closed position relative to the syringe barrel.

II. An Exemplary Syringe Apparatus

Figure 1:
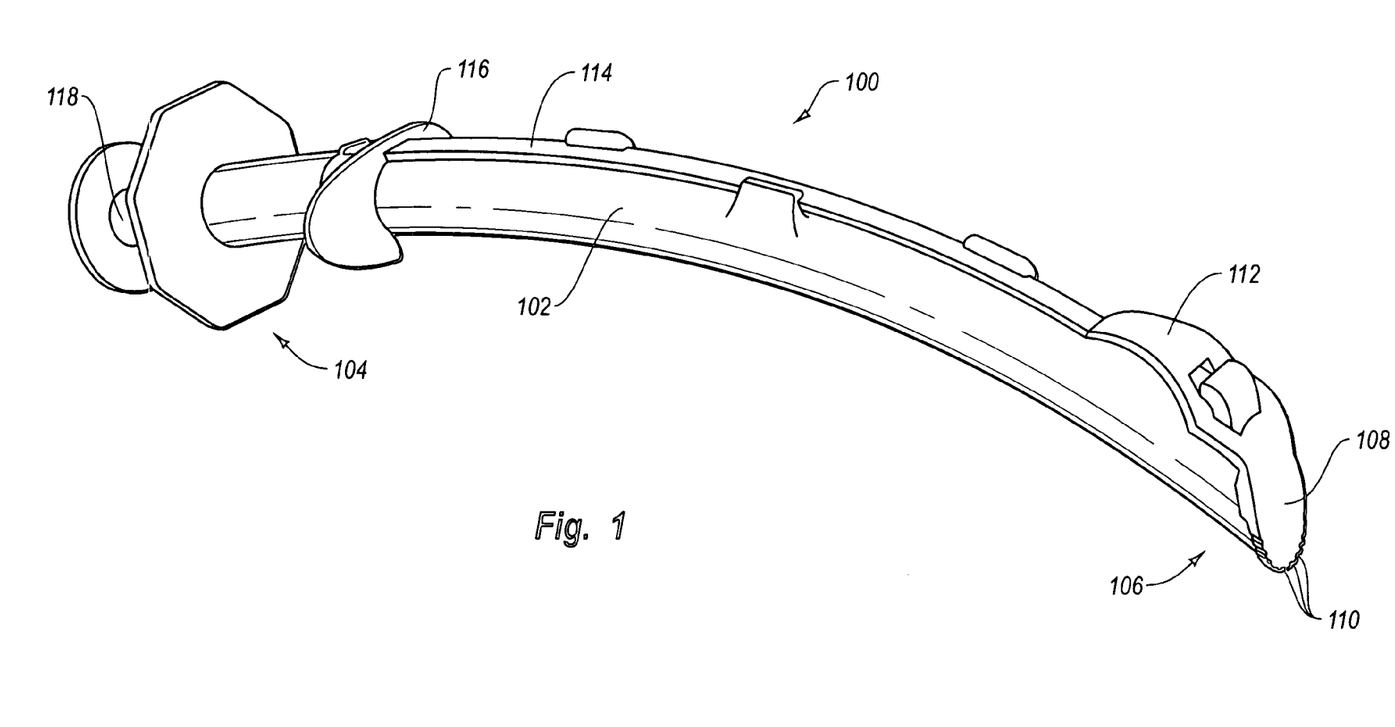
FIG. 1 is a perspective view of an exemplary syringe apparatus with the lid in a closed position relative to the syringe barrel.

FIG. 1 illustrates an exemplary syringe apparatus 100. Syringe apparatus 100 includes a syringe barrel 102 having a length extending between a proximal end 104 and a distal end 106. Like conventional syringe barrels commonly used in the art, syringe barrel 102 defines an interior chamber into which a material can be stored and into which a plunger can be slidably received for expelling the material from the syringe barrel 102. Syringe barrel 102 of FIG. 1 may be curved, as illustrated. A curved syringe barrel is generally advantageous in assisting the dental practitioner in maneuvering the apparatus 100 to deliver a granular or powdered material to a desired location within the mouth of a patient. Syringe barrel 102 may also include a distal end 106 that is beveled, as illustrated in FIG. 1.

The syringe apparatus 100 also includes a lid 108. Lid 108 is attached to syringe barrel 102 so as to be selectively movable between an open position and a closed position relative to the distal end 106 of syringe barrel 102. In the illustrated embodiment, lid 108 is hingedly attached to syringe barrel 102, although other attachments may alternatively be used. Because the lid 108 is hingedly attached to syringe barrel 102 it remains attached to the syringe barrel when moved between the open and closed positions (e.g., FIGS. 6 and 7).

According to one embodiment, lid 108 may include openings 110 within the lid 108. The openings 110 may comprise grooves, as illustrated in FIG. 1. Openings 110 result in a lid 108 that only partially obstructs an exit opening at distal end 106 of syringe barrel 102 so as to allow a dental practitioner to suction blood or other liquid into the syringe barrel 102 for mixing with a granular or powdered material contained therein, even when lid 108 is in a closed position. This may be advantageous as it provides a mixture that may be more easily delivered to the desired site (i.e., a slurry is generally more flowable than a dry powder or granules). Blood also makes the solid material more biologically compatible.

According to one embodiment where the syringe apparatus 100 is to be used with solid granules, the openings (e.g., grooves) 110 have a diameter that does not exceed the smallest granules to be used. For example, granules are often manufactured with a diameter greater than about 0.315 mm. According to one such embodiment, the openings 110 of lid 108 will have a diameter not greater than about 0.315 mm. This prevents loss of the granules through openings 110, while also allowing blood or other liquid to be suctioned through openings 110.

Figures 2, 3:
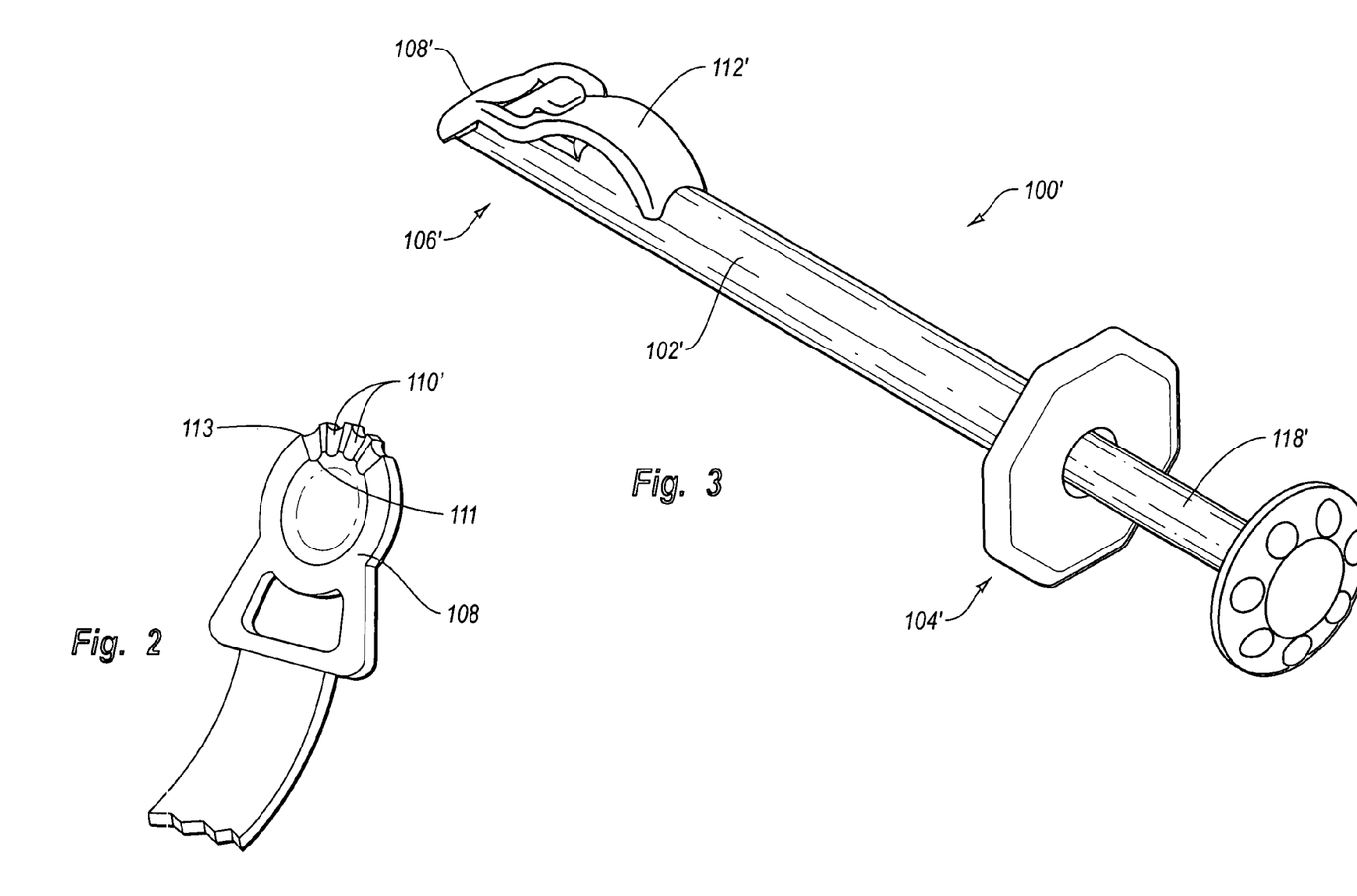
FIG. 2 is a perspective view of an alternative embodiment of a lid having outwardly tapered grooves for increased fluid flow.
FIG. 3 is a perspective view of an alternative exemplary syringe apparatus with the lid in an closed position relative to the syringe barrel.

According to an alternative embodiment shown in FIG. 2, the lid 108 may include tapered grooves 110' that taper outwardly away from the granule contact surface (i.e., the ends of the grooves 110' that contact granules within the syringe barrel 102). Providing grooves 110' that taper from a first end 111 closest to the granules within the syringe barrel toward a second end 113 opposite the granules provides for increased fluid flow of blood or other liquids through grooves 110' while still preventing the loss of granules within the syringe barrel 102 through the grooves 110'.

Syringe apparatus 100 also includes biasing means for biasing lid 108 toward a closed position relative to syringe barrel 102. According to one embodiment, the biasing means may comprise a leaf spring 112. Alternative biasing means may include other types of springs (e.g., a coiled spring), an elastomeric material positioned so as to be elastically compressed or stretched when opening the lid, and other biasing means known in the art.

Leaf spring 112 biases lid 108 in a closed position. In order to move lid 108 to an open position, a dental practitioner increases the effective length of the leaf spring, causing the lid 108 to open. This may be accomplished by pushing down on leaf spring 112 with a finger or thumb, or through use of means for remotely manipulating the leaf spring 112.

Syringe apparatus 100 may include opening means for remotely manipulating leaf spring 112. According to the illustrated embodiment, a pull-strap 114, which is shown extending along a portion of the length of syringe barrel 102, comprises opening means for selectively and remotely manipulating leaf spring 112. Pull-strap 114 is attached to one end of leaf spring 112 such that when a user pulls pull-strap 114 in a direction away from the distal end 106, the effective length of leaf spring 112 is increased, causing lid 108 to open (e.g., as in FIG. 7). Pull-strap 114 preferably includes a grip 116 near the proximal end 104 of syringe barrel 102. Releasing pull-strap 114 also releases leaf spring 112, which allows the lid 108 to return to its closed position (e.g., as in FIG. 6).

Syringe apparatus 100 also includes a plunger 118, which is used to expel materials from the barrel 102. It may also be used to suction blood into syringe barrel 102. According to one embodiment, plunger 118 may be flexible, preferably in both the x plane and the y plane. Exemplary embodiments of various plungers are shown in FIGS. 4A-5B, discussed below.

FIG. 3 illustrates an alternative embodiment of a syringe apparatus 100'. Syringe apparatus 100' includes a straight syringe barrel 102' having a proximal end 104' and a distal end 106'. Syringe apparatus 100' also includes a lid 108' and a leaf spring 112' for biasing the lid 108' towards the closed position relative to syringe barrel 102'. Syringe apparatus 100' is illustrated with a plunger 118'. This embodiment does not include a pull-strap attached to the lid 108'.

Figure 4A:
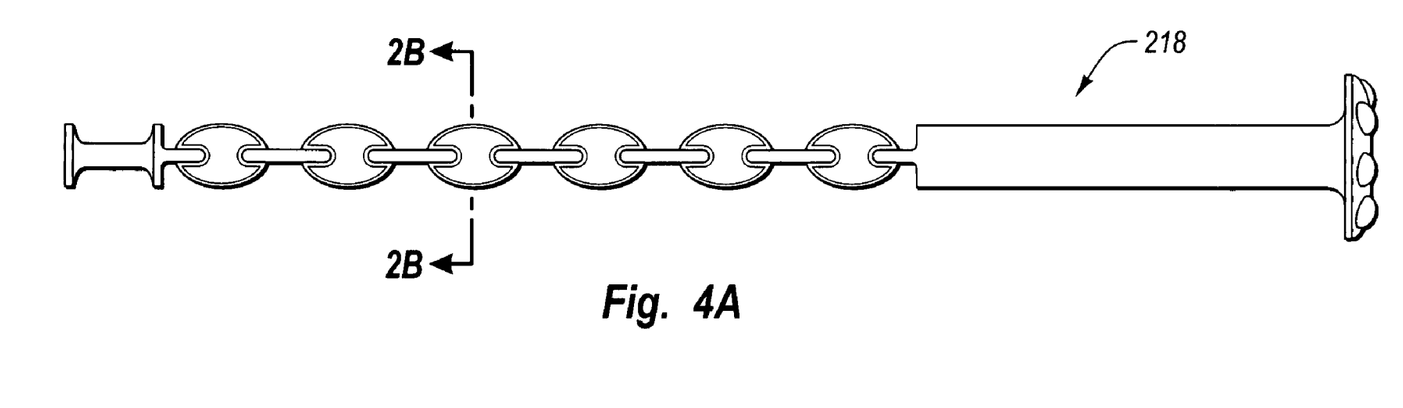
FIG. 4A is a perspective view of an exemplary plunger for use with the syringe apparatus of FIGS. 1 and 3.
Figure 4B:
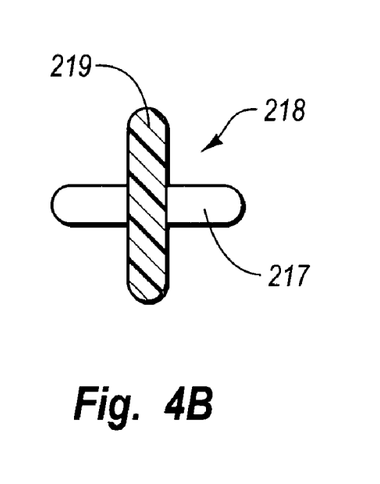
FIG. 4B is a cross-sectional view of the exemplary plunger of FIG. 4A.

FIG. 4A illustrates one embodiment of a flexible plunger 218. FIG. 4B illustrates a cross sectional view of plunger 218. As can be seen from FIGS. 4A and 4B, the plunger 218 has alternating sections of x plane and y plane flexibility. Section 217 provides flexibility in the x plane, while section 219 provides flexibility in the y plane.

Figure 5A:
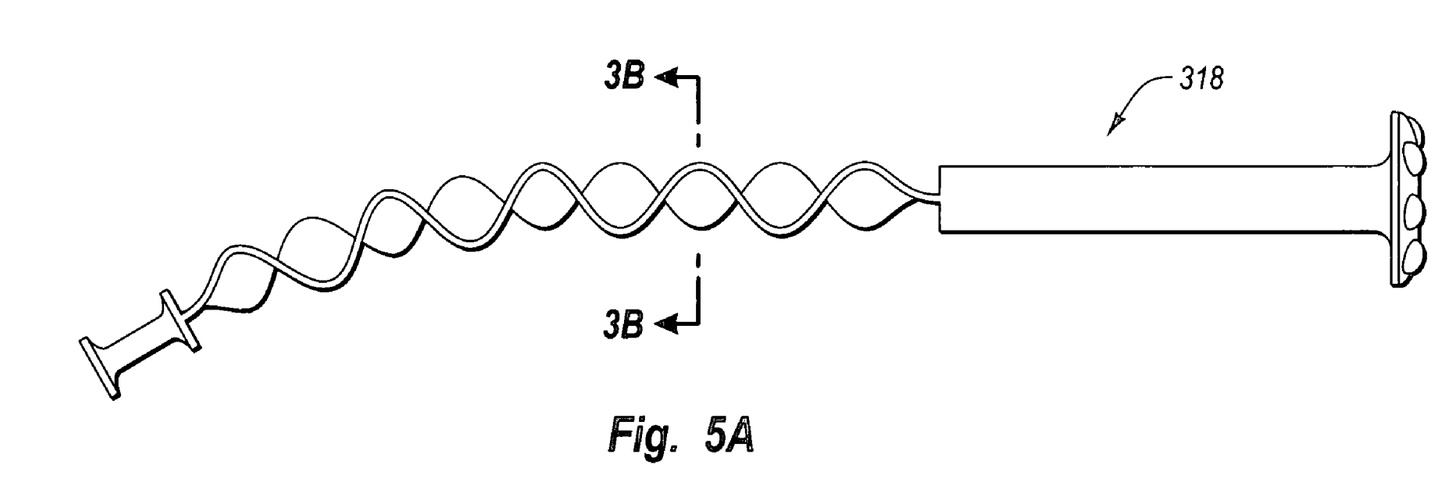
FIG. 5A is a perspective view of an alternative exemplary plunger for use with the syringe apparatus of FIGS. 1 and 3.
Figure 5B:
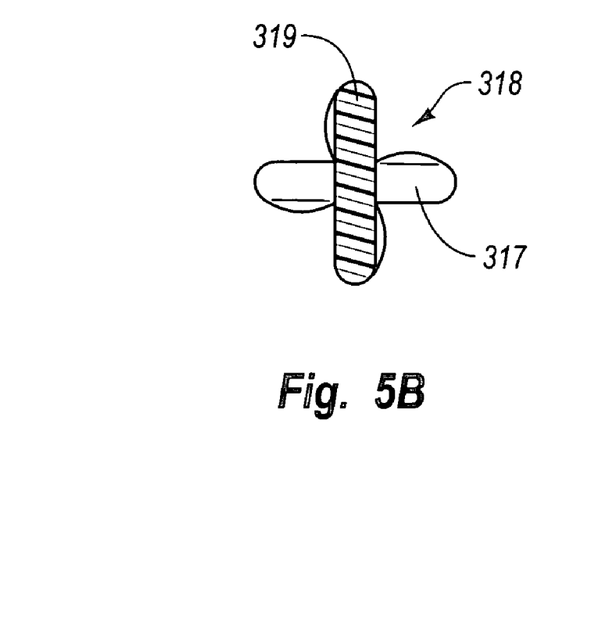
FIG. 5B is a cross-sectional view of the alternative exemplary plunger of FIG. 3.

FIG. 5A illustrates another embodiment of a flexible plunger 318. FIG. 5B illustrates a cross sectional view of plunger 318. As can be seen from FIGS. 5A and 5B, the plunger 318 has a different configuration, also providing flexibility within the x plane and the y plane. Section 317 provides flexibility in the x plane, while section 319 provides flexibility in the y plane. Although plunger 318 is shown as being curved, it may be curved or straight. Curved and/or flexible plungers may be preferred for use with a curved syringe barrel.

III. Exemplary Method of Use

The syringe apparatus may be used to dispense any granular or powdered material. One exemplary use is for delivering a granular or powdered bone growth promoting material, e.g., to preserve the alveolar portion of the jaw bone which supports the teeth. When a tooth is removed, the underlying portion of the jaw bone will contain a defect that can greatly weaken the bone. In addition, the bone may atrophy and weaken as a result of non-use and removal of the tooth. Implanting granular or powdered bone growth promoting material inhibits soft tissue growth and provides bone growth so as to strengthen the area of the jaw bone into which it is implanted.

Examples of granular or powdered bone growth promoting materials may include at least one of calcium hydroxyapatite, beta-tricalcium phosphate, purified coral shell, freeze-dried natural bone powder, freeze-dried natural bone particles, demineralized natural bone powder, and demineralized natural bone particles, shards or fragments.

Figure 6:
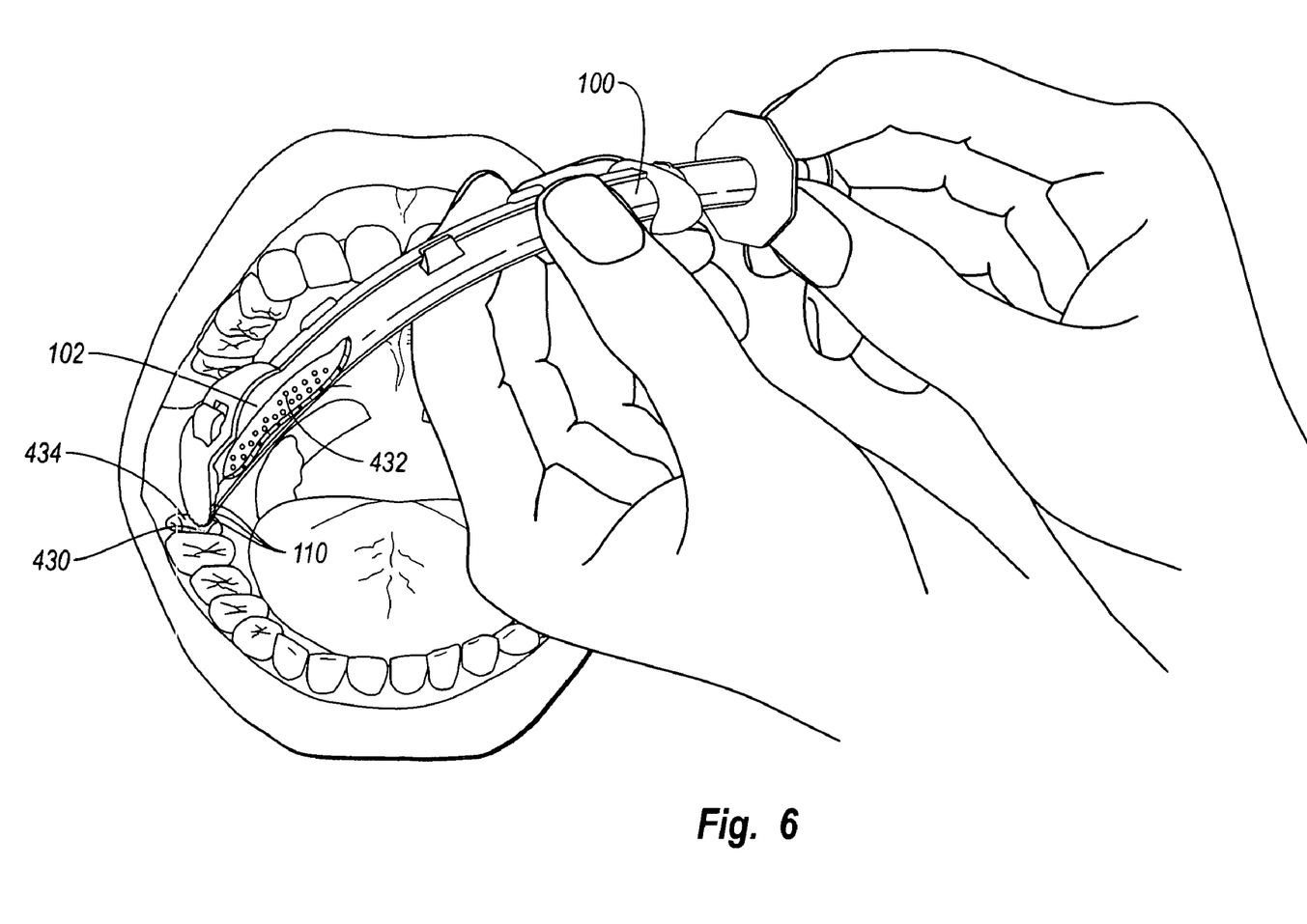
FIG. 6 is a perspective view of a tooth extraction site where an exemplary syringe apparatus is being used to suction blood into the syringe barrel for mixing with the granular or powered bone growth promoting material.

FIG. 6 is a perspective view of a portion of a patient's mouth where the third molar has just been removed, leaving behind a void 430. A syringe apparatus 100 is shown being used to suction blood 434 into the syringe barrel 102 for mixing with a granular or powdered bone growth promoting material 432. Blood 434 may be suctioned through grooves 110. Mixing the granular or powdered material 432 with blood 434 prior to delivering the material 432 into the void 430 may help in delivering the mixture more effectively and with less spillage. It also results in a more biocompatible material.

Figure 7:
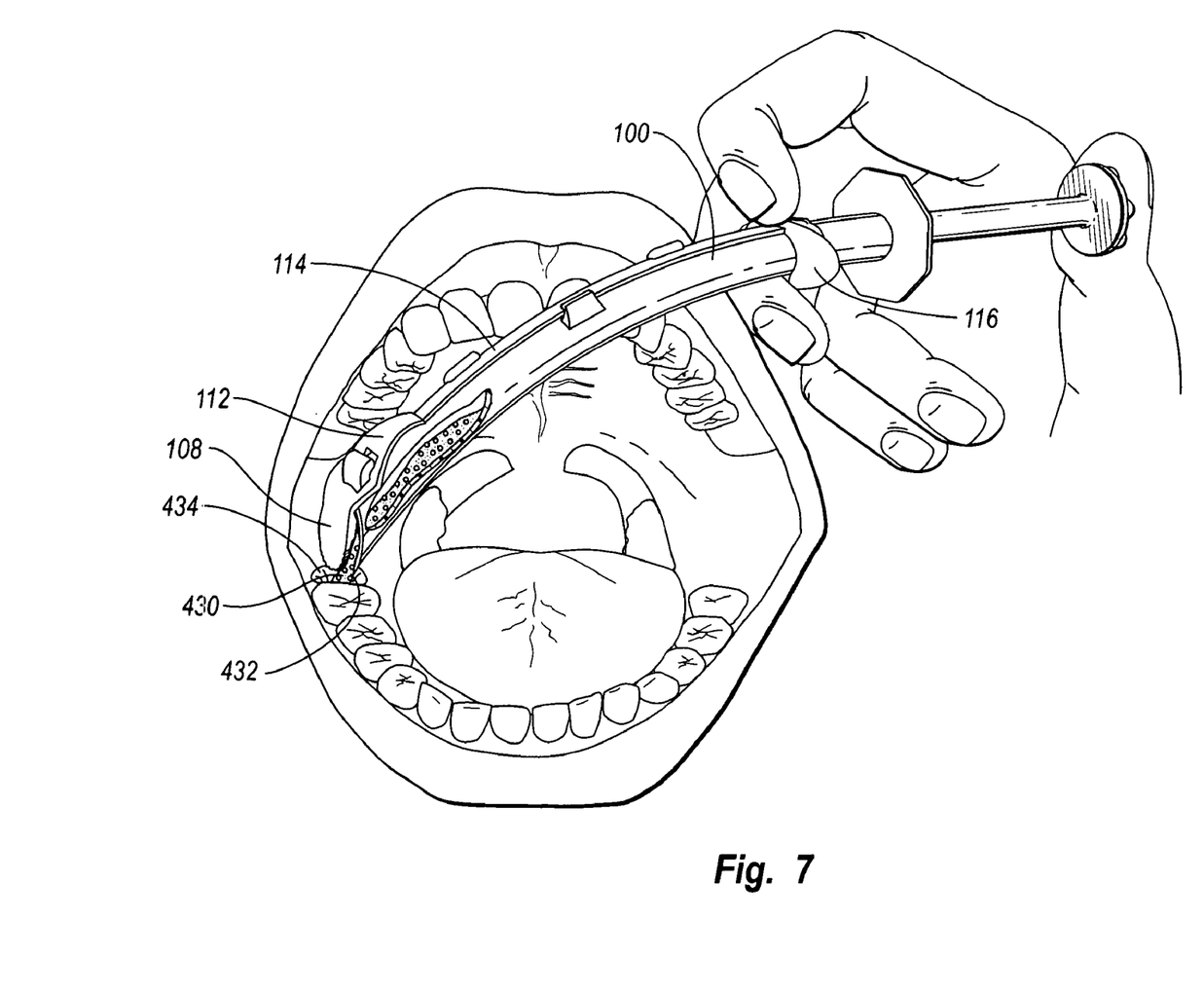
FIG. 7 illustrates use of the syringe apparatus of FIG. 4 to deliver a granular or powdered bone growth promoting composition mixed with blood.

As illustrated in FIG. 7, the syringe apparatus 100 is maneuvered as desired, and the granular or powdered material 432 is dispensed from the distal end of barrel 102 of the syringe apparatus 100 together with blood 434 into void 430 adjacent to the jaw bone tissue so as to selectively promote growth of the bone tissue and prevent the incursion of faster-growing soft tissue. The material 432 may be dispensed by opening lid 108, which is opened by manipulating leaf spring 112, either directly with a finger or thumb, or remotely with pull-strap 114 and grip 116, so as to permit passage of granular or powdered material 432 through an exit opening of the distal end of barrel 102.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A syringe apparatus for delivering a granular or powdered material, comprising:
    a syringe barrel having a proximal end and a distal end;
    an exit opening at the distal end of the syringe barrel;
    a lid attached to the syringe barrel that is selectively movable between an open position in which the lid permits passage of granular or powdered material through the exit opening and a closed position relative to the syringe barrel,
       the lid remaining attached to the syringe barrel when moved between the open and closed positions;
       the lid including openings for allowing a user to suction blood or liquid into the syringe barrel for mixing with the granular or powdered material; and
    biasing means for biasing the lid toward the closed position relative to the syringe barrel.

2. A syringe apparatus as recited in claim 1, further comprising a plunger disposed within the syringe barrel and configured to expel material from the syringe barrel.

3. A syringe apparatus as recited in claim 2, wherein the plunger is flexible.

4. A syringe apparatus as recited in claim 2, wherein the plunger is flexible in both the x plane and the y plane.

5. A syringe apparatus as recited in claim 2, wherein the plunger is longitudinally curved.

6. A syringe apparatus as recited in claim 1, wherein the syringe barrel is longitudinally curved.

7. A syringe apparatus as recited in claim 1, wherein the distal end of the syringe barrel is beveled.

8. A syringe apparatus as recited in claim 1, wherein the lid is hingedly attached to the syringe barrel.

9. A syringe apparatus as recited in claim 1, wherein the openings have a diameter not greater than about 0.315 mm.

10. A syringe apparatus as recited in claim 1, wherein the openings comprise grooves.

11. A syringe apparatus as recited in claim 10, wherein the grooves are tapered.

12. A syringe apparatus as recited in claim 1, wherein the biasing means comprises a leaf spring for biasing the lid toward a closed position relative to the syringe barrel.

13. A syringe apparatus as recited in claim 12, further comprising means for remotely manipulating the leaf spring so as to move the lid to an open position relative to the syringe barrel.

14. A syringe apparatus as recited in claim 13, wherein the means for remotely manipulating the leaf spring comprises a pull-strap attached to the leaf spring.

15. A syringe apparatus as recited in claim 14, wherein the pull-strap includes a grip near the proximal end of the syringe barrel.

16. A syringe apparatus for delivering a granular or powdered material, comprising:
    a syringe barrel having a length extending between a proximal end and a distal end, the syringe barrel further defining an interior chamber into which a material can be stored and into which a plunger can be slidably received for expelling the material from the syringe barrel;
    an exit opening at the distal end of the syringe barrel;
    a lid attached to the syringe barrel that is selectively movable between an open position in which the lid permits passage of granular or powdered material through the exit opening and a closed position relative to the syringe barrel in which the lid retains granular or powdered material within the syringe barrel,
       the lid remaining attached to the syringe barrel when moved between the open and closed positions;
    a leaf spring disposed at the distal end of the syringe barrel and cooperating between the syringe barrel and the lid in order to bias the lid toward the closed position relative to the syringe barrel; and
    opening means, extending along a portion of the length of the syringe barrel, for selectively and remotely manipulating the leaf spring by gripping the opening means at a position along the length of the syringe barrel so as to move the lid to an open position relative to the syringe barrel by pulling the opening means, the lid returning to its closed position over the distal end upon release of the opening means.

17. A syringe apparatus as recited in claim 16, wherein the means for remotely manipulating the leaf spring comprises a pull-strap attached to the leaf spring.

18. A syringe apparatus as recited in claim 17, wherein the pull-strap includes a grip near the proximal end of the syringe barrel.

19. A syringe apparatus for delivering a granular or powdered material, comprising:
 a syringe barrel having a proximal end and a distal end;
 an exit opening at the distal end of the syringe barrel;
 a lid attached to the syringe barrel that is selectively movable between an open position in which the lid permits passage of granular or powdered material through the exit opening and a closed position relative to the syringe barrel,
  the lid remaining attached to the syringe barrel when moved between the open and closed positions; and
 openings within the lid that allow a user to suction blood or liquid into the syringe barrel.

20. A syringe apparatus as recited in claim 19, wherein the openings comprising outwardly tapered grooves.

21. A method for delivering a granular or powdered material comprising:
 providing a syringe apparatus as recited in any of claims 1, 16 or 19; and
 dispensing a granular or powdered bone growth promoting material from the syringe apparatus adjacent to bone tissue to be augmented.

22. A method as recited in claim 21, wherein the granular or powdered bone growth promoting material is dispensed into a void or defect resulting from the removal of a tooth.

23. A method as recited in claim 21, wherein the granular or powdered bone growth promoting material comprises at least one of calcium hydroxyapatite, beta-tricalcium phosphate, purified coral shell, freeze dried natural bone powder, freeze dried natural bone particles, demineralized natural bone powder, or demineralized natural bone particles, shards or fragments.

24. A method as recited in claim 21, further comprising mixing the granular or powdered bone growth promoting material with blood prior to dispensing the bone growth promoting material from the syringe apparatus adjacent to bone tissue to be augmented.

* * * * *

UNITED STATES PATENT AND TRADEMARK OFFICE
CERTIFICATE OF CORRECTION

| | | |
|---|---|---|
| PATENT NO. | : 7,357,789 B2 | Page 1 of 1 |
| APPLICATION NO. | : 10/995571 | |
| DATED | : April 15, 2008 | |
| INVENTOR(S) | : Bills | |

It is certified that error appears in the above-identified patent and that said Letters Patent is hereby corrected as shown below:

Column 7
Line 18, change "comprising" to --comprise--

Signed and Sealed this

First Day of December, 2009

David J. Kappos
*Director of the United States Patent and Trademark Office*